(12) United States Patent
McKenna et al.

(10) Patent No.: US 7,462,733 B2
(45) Date of Patent: Dec. 9, 2008

(54) PREPARATION AND USE OF α-KETO PHOSPHONATES

(75) Inventors: Charles E. McKenna, Pacific Palisades, CA (US); Boris A. Kashemirov, Los Angeles, CA (US); Patricia I. Bonaz-Krause, Oakland, CA (US)

(73) Assignee: University of Southern California, Los Angeles, CA (US)

( * ) Notice: Subject to any disclaimer, the term of this patent is extended or adjusted under 35 U.S.C. 154(b) by 497 days.

(21) Appl. No.: 10/481,071

(22) PCT Filed: Jul. 30, 2002

(86) PCT No.: PCT/US02/24213

§ 371 (c)(1),
(2), (4) Date: May 28, 2004

(87) PCT Pub. No.: WO03/011221

PCT Pub. Date: Feb. 13, 2003

(65) Prior Publication Data

US 2004/0236135 A1 Nov. 25, 2004

Related U.S. Application Data

(60) Provisional application No. 60/308,909, filed on Jul. 30, 2001.

(51) Int. Cl.
C07F 9/02 (2006.01)
C07H 19/04 (2006.01)

(52) U.S. Cl. .................. 558/160; 558/152; 558/155; 536/26.1; 536/26.2

(58) Field of Classification Search .................. 558/160, 558/152, 155
See application file for complete search history.

(56) References Cited

U.S. PATENT DOCUMENTS 6,147,245 A * 11/2000 McKenna et al. ........... 558/145
6,148,245 A 11/2000 McKenna et al.

FOREIGN PATENT DOCUMENTS

| GB | WO1996006844 | 3/1996 |
| WO | WO1994029331 | 12/1994 |
| WO | WO1996022778 | 8/1996 |
| WO | WO1999025352 | 5/1999 |

OTHER PUBLICATIONS

Ebetino, F.H. Phosphorusm Sulfur Silicon Relat. elem 1999 144-146, 9-12.
De Clercq, E. 2001 Current Medicinal Chemistry 8, 1543-1572.
De Clerq E. 2002 Nature Reviews Drug Discovery 1, 13-25.
Hamilton, C.J., Roberts, S.M. and Shipitsin, A. 1998 Chem. Commun. (Cambridge) 1087-1088.
Blazarini, J., Haller-Meier, F., De Clercq, E. and Meier, C. 2001 Antiviral Chemistry & Chemotherapy 12, 301-306.
Parang, K. , Wiebe, L.I. and Knaus, E.E. 2000 Curr. Med. Chem. 7, 995-1039.
Ohrui, H. and Mitsuya, H. 2001 Curr. Drug Targets: Infect. Discord. 1, 1-10.
Debyser, Z. and De Clercq, E. 1996 Riv. Immunol. Immunofarmacol. 16, 48-52.
Davisson, V.J., Davis, D.R., Dixit, V.M. and Poulter, C.D. 1987 J. Org. Chem. 52, 1794-1801.
McLennean, A.G., Taylor, G.E., Prescott, M. and Blackburn, G.M. 1989 Biochemistry 28, 3868-3875.
Lesiak, K., Watanabe, K.A., Majumdar, A., Seidman, M., Vanderveen, K., Goldstein, B.M. and Pankiewicz, K.W. 1997 J. Med. Chem. 40, 2533-2538.
Balzarini, J., Herdewijn, P., Pauwels, R., Broder, S. And De Clercq, E. 1988, Biochem. Pharacol. 37, 2395-2403.
Guranowski, A., Starzynska, E., Gzik, L., Langston, S.P., Brown P. and Blackburn, G.M. 1995 Nucleosides Nucleotides 14, 731-734.
Blackburn, G.M. and Langston, S.P. 1991 Tetrahedron Lett. 32, 6425-6428.
Blackburn, G.M., Kent, D.E. and Kolkmann, F. 1984 J. Chem. Soc., Perkin Trans. 1 1119-1125.
Burton, D.J., Pietrzyk, D.J., Ishihara, T., Fonong, T. and Flynn, R.M. 1982 J. Fluorine Chem. 20, 617-626.
Cox, G.G., Miller, D.J., Moody, C.J., Sie, E., Kulagowski, J.J. Tetrahedron 1994, 50, 3195-3212.
Shapiro, E.A., Dyatkin, A.B., Nefedov, O.M. Russian Chemical Reviews 1993, 62, 485-509.
Brown, D.S., Elliott, M.C., Moody, C.J., Mowlem, T.J., Marion JR., J.P., Padwa, A. J. Org. Chem. 1993, 59, 2447-2455.
McKenna, C.E., Levy, J.N.J. Chem. Soc., Chem. Comm. 1989, 246-247.
McKenna, C.E., Kashemirov, B.A. And Li, Z.M. 1999, Phosphorous, Sulfur Silicon Relat. Elem. 144-146, 313-316.
McKenna, C.E., Higa, M.T., Cheung, N.H. And McKenna, M.C. 1977 Tetrahedron Lett. 155-158.
McKenna, C.E. And Schmidhauser, J. 1979 J. Chem. Soc., Chem. Commun. 739.
Rasanen, J.P., Pohjala, E., Nikander, H. And Pakkanen, T.A. 1996 J. Phys. Chem. 100, 8230-8239.
Rasanen, J.P., Pohjala, E. And Pakkanen, T.A. 1996 J. Chem. Soc., Perkin Trans. 2 39-47.
Rasanen, J.P., Pohjala, E. And Pakkanen, T.A. 1994 J. Chem. Soc., Perkin Trans. 2 2485-2490.
Rasanen, J.P., Pohjala, E., Nikander, H. And Pakkanen, T.A. 1997 J. Phys. Chem. A 101, 5196-5204.
Yanachkov, I.B., Stattel, J.M. And Wright, G.E. 2001 J. Chem. Soc., Perkin Trans. 1 3080-3089.
Khare, A.B., McKenna, C.E. Synthesis 1991, 405-406.
Campagne, J.M., Coste, J. And Jouin, P. 1995 J. Org. Chem. 60, 5214-5223.
Campbell, D.A. 1992 J. Org. Chem. 57, 6331-6335.
Campbell, D.A. And Bermak, J.C. 1994 J. Org. Chem. 59, 658-660.
Kashemirov, B.A., Rose, C.N. And McKenna, C. 2001 Campbell, XVth International Conference on Phosphorus Chemistry PA017.
Kashemirov, B.A. And McKenna, C. 2002 Topics Curr. Chem. 220, 201-238.

* cited by examiner

*Primary Examiner*—Joseph McKane
*Assistant Examiner*—Yong Chu
(74) *Attorney, Agent, or Firm*—Fulbright & Jaworski LLP (57) ABSTRACT

Novel phosphonate compounds are provided including a phosphonoglyoxylamide ester, an α-keto phosphonophosphinate ester, a carbonylbisphosphonate analog of a nucleotide, and a diazomethylenebisphosphonate analog of a nucleotide, as well as methods of making synthetically and medically useful α-keto phosphonate compounds.

6 Claims, 4 Drawing Sheets

PREPARATION AND USE OF α-KETO PHOSPHONATES

RELATED APPLICATIONS

This application claims the benefit of U.S. provisional application No. 60/308,909 filed on Jul. 30, 2001

BACKGROUND OF THE INVENTION

In recent years, many investigators have shown interest in the method of synthesis and biological activity of bisphosphonates and their derivatives, which can be regarded as analogues of natural pyrophosphates. Pyrophosphates are known to be natural regulators of $Ca^{2+}$ metabolism at the cellular level and form many nucleotides. Synthetic analogues of pyrophosphates, namely bisphosphonates, are not metabolized because their P—C—P bonds are less labile than the P—O—P linkage of natural pyrophosphates.

The elucidation and further development of structure-activity relationships in the bisphosphonate class of compounds has increasingly flourished during the past few years, as recently reviewed by Ebetino(1). Rational design of new medicinal agents based on bisphosphonates has progressed from simple α-alkyl and α-halo bisphosphonates, to bisphosphonates substituted with a range of heterocyclic and heteroatomic moieties. Bisphosphonate chemistry has yielded an increasing variety of bone-active compounds, including potent antiresorptive agents that have therapeutic potential in osteoporosis and other diseases of bone metabolism. Variation in the P—C—P backbone has led to analogues of varied hydroxyapatite affinity, $Ca^{2+}$ chelation and antimineralization properties.

Current theory attributes the biological activity of antiresorptive bisphosphonates to two design components. One of these is the so-called 'bone hook' functionality, associated with the bisphosphonate backbone, e.g., in [$(HO)_2P(O)CR(OH)P(O)(OH)_2$], all of the molecule except the "R" substituent. This functionality is directly responsible for primary hydroxyapatite adsorption. A second "bioactive" moiety is postulated to modulate the anti-resorptive potency of the drug within a given affinity class.

It should be noted that α-hydroxy bisphosphonates possess high affinity for hydroxyapatite and include some of the most potent antiresorptive agents, thus chemistry that generates an α-hydroxy function together with addition of the R group is particularly desirable. Indeed the compound hydroxyethylidenediphosphonic acid (HEDP) $(HO)_2P(O)CCH_3(OH)P(O)(OH)_2$, where $R=CH_3$ is one of the best known bisphosphonates used in medicine under the name Etidronate (disodium salt of HEDP). HEDP is a useful complexing agent for alkaline earth, transition, and lanthanide metals, can be used to regulate calcium metabolism in the treatment of Paget's disease, inhibits formation and growth of calcium oxalate stones in kidneys, can reduce plaque when added to dental preparations, and has been indicated for treatment of diseases ranging from bone cancer to osteoporosis and arthritis.

Design and synthesis of new bisphosphonate containing drugs active against bone diseases would be greatly aided by preparative methodology facilitating introduction of the "R" moiety into the bisphosphonate structure. Such methodology, should it be available, could also be employed for preparation of bisphosphonates that might be useful in treating many other diseases, such as viral infections, or other health disorders that may be responsive to phosphonate drugs.

One such useful modification might include modified nucleosides, which have acquired an important role as therapeutic agents in the treatment of diseases caused by infectious viruses such as human immunodeficiency virus (HIV), or herpes viruses (2,3). Despite the advent of potent new antiviral nucleoside analogues such as carbovir (4) and abacavir (5,6), AZT (3'-azido-3'-deoxythymidine) continues to play an important role in the chemotherapy of AIDS (7-9), particularly in combination with other HIV reverse transcriptase (RT) nucleoside analogue inhibitor (NRTI), non-nucleoside reverse transcriptase inhibitors (NNRTI), and HIV protease inhibitors (10-11).

α,β-methylene analogues of nucleoside diphosphates (12-15) or β,γ-methylene analogues of nucleoside triphosphates (4, 16-19) have been previously studied. Replacement of the anhydride oxygen by the less electronegative carbon atom increases the P—OH pKa values; however this can be addressed by fluorine substitution (20). Replacement of the anhydride oxygen by a reactive carbon group, which is also sterically minimal and electronegative, represents a more challenging problem.

SUMMARY OF THE INVENTION

The present invention provides a series of novel phosphonate compounds, such as a phosphonoglyoxylamide ester, an α-keto phosphonophosphinate ester, a carbonylbisphosphonate analog of a nucleotide, and a diazomethylenebisphosphonate analog of a nucleotide.

These include the phosphonoglyoxylamide ester of formula I:

and the phosphonophosphinate ester of claim 1 having formula II:

wherein R1, R2, R3 and R4 are each independently selected from the group consisting of alkyl and aryl.

The nucleotide analogs are generally of formula III:

wherein Y is oxygen or diazo, R1, R2, R3 and R4 are each independently selected from the group consisting of hydrogen, alkyl aryl, and nucleosidyl and at least one of R1, R2, R3 and R4 is a nucleoside (or nucleoside analog) coupled to the bisphosphonate via a 5' ester linkage.

The present invention further provides a method of preparing α-keto phosphonates, which includes the steps of (1) forming a reaction mixture comprising an a rhodium(II) cata lyst, an oxygen donor and an α-diazo phosphonate having formula IV:

wherein X is selected from the group consisting of —C(=O)OR3, —C(=O)N(R4)(R5), and —P(=O)(OR6)(R7), wherein R1, R2 R3, R4, R5 and R6 and each independently selected from the group consisting of alkyl, and aryl; R7 is selected from the group consisting of alkyl, aryl, and OR8, wherein R8 is selected from the group consisting of alkyl, aryl and nucleosidyl; and (2) oxidizing the α-diazo phosphonate to form an α-keto phosphonate.

Another method of preparing α-keto phosphonates includes the steps of: (1) forming a reaction mixture comprising tert-butyl hypochlorite, a polar aprotic solvent and an α-diazo phosphonate having formula VI:

wherein X is selected from the group consisting of —C(=O)OR3, —C(=O)NR4R5, and —P(=O)OR6R7, wherein R1, R2 R3, R4, R5 and R6 and each independently selected from the group consisting of alkyl, and aryl; R7 is selected from the group consisting of alkyl, aryl, and OR8, wherein R8 is selected from the group consisting of alkyl, aryl and nucleosidyl; and (2) adding an effective amount of water to said reaction mixture, whereby the α-diazo phosphonate is converted to an α-keto phosphonate.

Another version of the present invention provides a method of preparing a nucleotide analog, which includes the steps of forming a monosalt of an α-diazomethylenebisphosphonate; and coupling a nucleoside and the monosalt to form a nucleotide analog having formula VII:

wherein R1, R2 and R4 are each independently alkyl or aryl and R3 is a nucleosidyl moiety joined to the bisphosphonate via a 5'ester linkage. The method can further comprise the step of oxidizing the diazomethylene bisphosphonate to form a carbonylbisphosphonate.

DETAILED DESCRIPTION

The present invention provides a series of novel phosphonate compounds, including a phosphonoglyoxylamide ester, an α-keto phosphonophosphinate ester, a carbonylbisphosphonate analog of a nucleotide, and a diazomethylenebisphosphonate analog of a nucleotide.

The phosphonoglyoxylamide ester is generally of formula I:

wherein R1, R2, R3 and R4 are each independently selected from the group consisting of alkyl and aryl. Preferred alkyl groups include methyl, ethyl, butyl, and propyl.

The phosphonophosphinate ester is generally of formula II:

wherein R1, R2, R3 and R4 are each independently selected from the group consisting of alkyl and aryl.

The carbonylbisphosphonate or diazomethylenebisphosphonate analogs of nucleotides are generally of formula III:

wherein Y is oxygen or diazo, R1, R2 and R4 are each independently selected from the group consisting of hydrogen, alkyl and aryl, and R3 is a nucleosidyl or nucleosidyl analog moiety. Preferably the nucleotide analog includes a modified purine or pyrimidine base residue with useful medicinal properties, such as 5-fluorouracil. Similarly, preferred versions can include a modified ribosyl or deoxyribosyl residue. A most preferred version is a compound wherein the nucleosidyl analog moiety is 3'-azido-3'deoxythymidinyl.

Another version of the present invention further provides a method of preparing α-keto phosphonates, which includes the steps of (1) forming a reaction mixture comprising an a rhodium(II) catalyst, an oxygen donor and an α-diazo phosphonate having formula IV:

wherein X is selected from the group consisting of —C(=O)OR3, —C(=O)N(R4)(R5), and —P(=O)(OR6)(R7), wherein R1, R2 R3, R4, R5 and R6 and each independently selected from the group consisting of alkyl, and aryl; R7 is selected from the group consisting of alkyl, aryl, and OR8, wherein R8 is selected from the group consisting of alkyl, aryl and nucleosidyl; and (2) oxidizing the α-diazo phosphonate to form an α-keto phosphonate.

The oxygen donor is typically an alkene oxide, such as propylene oxide, 1,2-epoxybutane, 1,2-expoxyhexane and styrene oxide. When X is —C(═O)N(R4)(R5), a most preferred oxygen donor is styrene oxide.

Rhodium (II) catalysts with donor ligands, which can include $Rh_2(NHCOC_3F_7)_4$, $Rh_2(OCOCH_3)_4$, $Rh_2(CF_3CONH)_4$, and $Rh_2(CH_3CONH)_4$. The preferred catalyst is $Rh_2(NHCOC_3F_7)_4$, however in one version of the method the catalyst can be $Rh_2(OCOCH_3)_4$ when X is —C(═O)N(R4)(R5).

Another version of the present invention is a method of preparing α-keto phosphonates, which includes the steps of: (1) forming a reaction mixture comprising tert-butyl hypochlorite, a polar aprotic solvent and an α-diazo phosphonate having formula VI:

wherein X is selected from the group consisting of —C(═O)OR3, —C(═O)NR4R5, and —P(═O)OR6R7, wherein R1, R2, R3, R4, R5 and R6 are each independently selected from the group consisting of alkyl, and aryl; R7 is selected from the group consisting of alkyl, aryl, and OR8, wherein R8 is selected from the group consisting of alkyl, aryl and nucleosidyl; and (2) adding an effective amount of water to said reaction mixture, whereby the α-diazo phosphonate is converted to an α-keto phosphonate.

McKenna et al (21) previously described synthesis of 4 ester preparations by reaction of the corresponding α-diazo compounds with tert-butyl hypochlorite (See Scheme 1, Pathway A). Although the hypochlorite method conveniently produces carbonylbisphosphonate esters under very mild conditions, it suffers from two potential drawbacks: 1) the exothermicity and exponential increase in rate of reaction, so convenient on small scale, might pose cooling and control problems on major scale-up; 2) thus far, an efficient separation method to remove the small amount of dichlorinated side product always present, has not been found; 3) very precise control of reaction conditions is required, particularly in the water addition and excess water quenching steps.

The following compounds were synthesized as shown in Scheme 1 and the results are summarized in Table 1.

1, 3, 5, 7

2, 4, 6, 8

| 1 | R = Et, X = N₂, Y = OEt |
| 3 | R = Et, X = O, Y = OEt |

-continued 1, 3, 5, 7

2, 4, 6, 8

| 5 | R = Et, X = N₂, Y = NMe₂ |
| 7 | R = Et, X = O, Y = NMe₂ |
| 2 | R₁ = R₂ = R₃ = OiPr, X = N₂ |
| 4 | R₁ = R₂ = R₃ = OiPr, X = O |
| 6 | R₁ = R₂ = OEt, R₃ = Ph, X = N₂ |
| 8 | R₁ = R₂ = OEt, R₃ = Ph, X = O |

Scheme 1

Pathway A[1]:

Pathway B[2]:

Pathway C[3]:

1. Previously shown for the conversion of 2 to 4: C. E. McKenna and B. A. Kashemirov, "Preparation and Use of α-Keto Bisphosphonates", U.S. Pat. No. 6,147,245 (Nov. 14, 2000).
2. Previously shown for the conversion of 1 to 3; 2 was not converted to 4: C. E. McKenna and J. N. Levy, J. Chem. Soc., Chem. Commun., 1989 (4), 246-247; C. E. McKenna and J. N. Levy, unpublished data.
3. Catalyst prepared according to Brown et al., J. Org. Chem. 59, 2447 (1994).

TABLE 1

α-Diazo Phosphonate Oxidative Reactivities

| Diazo substrates | Pathway A | Pathway B | Pathway C |
|---|---|---|---|
| EtO\O N₂ O<br>  \\|| ||  ||<br>   P—C—C—OEt<br>  /<br>EtO<br>1 | + | +[a] | +[b] |

TABLE 1-continued

α-Diazo Phosphonate Oxidative Reactivities

| Diazo substrates | Pathway A | Pathway B | Pathway C |
|---|---|---|---|
| EtO-P(=O)(OEt)-C(N₂)-C(=O)-NMe₂  (5) | + | +[a] | +[b] |
| i-Pr-O-P(=O)(O-iPr)-C(N₂)-P(=O)(O-iPr)(O-iPr)  (2) | + | − | +[c] |
| EtO-P(=O)(OEt)-C(N₂)-P(=O)(OEt)(Ph)  (6) | + | − | +[c] |

[a]. Overnight in refluxing benzene; propylene oxide.
[b]. Sev. min to 1/2 hr at room temperature; styrene oxide.
[c]. Overnight in toluene at 100° C.; 1,2-epoxyhexane.
Plus indicates quantitative oxidation; minus indicates NR.

Our new approach to the synthesis of α-keto phosphonates 3, 4, 7, 8 provides a versatile pathway to new α-substituted bisphosphonate derivatives and could be readily adapted to combinatorial drug discovery synthetic strategies. It should be pointed out that conversion of the product adducts, which are esters, to corresponding acids, could be effected in a variety of ways known to skilled practitioners, from classical acid hydrolysis to much milder silyldealkylation with reagents such as bromotrimethylsilane. The method is particularly conducible to scaled up synthesis and generally affords distillable, analytical pure products. Additionally it avoids the use of water.

This new approach is based on discoveries of efficient general methods of oxidation of α-diazophosphonates by epoxides in presence of Rh(II) catalyst. It is known, that diazocarboxylate esters can be transformed by transition metal catalysts such as rhodium(II) acetate into alkoxycarbonylcarbenes that undergo a wide variety of synthetically useful C—H, C—C, C—X, X—H and X—X insertion reactions (where X=heteroatom)(22,23). Chemoselectivity of rhodium carbenoids derived from Rh(II) carboxylates and carboxamides has been found to exhibit striking ligand dependency, for example in work by Padwa (24) showing that perfluorocarboxamide ligands exclusively promoted aromatic C—H insertions in Rh(II)-catalyzed decomposition of diazoamides to give oxindoles, whereas a carboxylate-based rhodium catalyst promoted other types of insertions and addition reaction.

It was previously shown that Rh(II) acetate-propene oxide smoothly converts α-diazo phosphonoacetate esters (25) to the α-ketone. However, replacement of the carboxylate group in this diazo substrate by a second phosphonate moiety produces a dramatic drop in reactivity. The phosphonate group is strongly electron-withdrawing, but unlike the carboxylate substituent is unable to provide a stabilizing π-electronic interaction with the diazomethylene group as the latter begins to react with the Rh catalyst.

Thus, we found that tetraalkyl diazomethylenebisphosphonate esters are completely unreactive to rhodium acetate/propylene oxide, even after days of reflux in benzene, although these conditions give smooth conversion of triethyl diazophosphonoacetate to triethyl phosphonoglyoxylate in a few hours. Efforts to utilize more rigorous conditions (higher boiling epoxide and solvent) with this catalyst only confirmed the inertness of tetraisopropyl diazomethylenebisphosphonate.

The effect of the Rh(II) carboxylate catalyst ligand structure on rhodium-carbenoid mediated O—H insertions in catalytic decomposition of various diazo compounds in the presence of hydroxylic compounds has been studied by Cox et al.(22), who found that in this reaction, effectiveness varied with ligand, with L=CF₃CONH>CH₃CONH>CH₃CO, although no clear explanation of this order has been given. A problem with the trifluorocetamide catalyst is that it has not been well purified or characterized, and as obtained may consist of more than one species. In contrast, rhodium perfluorobutyramide [Rh₂(NHCOC₃F₇)₄] can be isolated as a well-defined compound, although it has not been used previously with diazomethylenephosphonate substrates.

Surprisingly, we discovered that the latter catalyst is highly effective in converting tetraisopropyl diazomethylenebisphosphonate to the carbonylbisphosphonate, using 1-hexene epoxide as the oxygen donor in refluxing benzene. The ketone product is obtained in high yield, and can be distilled under reduced pressure producing an analytically pure sample free of NMR-detectable impurities. This catalyst is also highly effective in the parallel synthesis of other novel trifunctional α-keto phosphonates, namely diethyl N,N-dimethyl phosphonoglyoxylamide (formed overnight at room temperature) and the mono(phenylphosphinate) analogue of tetraethyl carbonylbisphosphonate. Further showing its greatly enhanced activity relative to rhodium acetate in these reactions, rhodium perfluorobutyramide is found to be capable of converting triethyl α-diazo phosphonoacetate in benzene to triethyl phosphonoglyoxylate at room temperature in a few hours.

In addition, we have obtained the previously unexpected result that the oxygen donor—the oxirane ring—can significantly influence the overall rate of the reaction. Thus, when propylene oxide is replaced in the oxidation of diethyl N,N-dimethyl phosphonoglyoxylamide by an epoxide configured to provide stabilizing delocalization of charge developed during ring-opening—styrene oxide—the conversion, which requires overnight using propylene oxide, occurs at room temperature within a few minutes

α-Ketophosphonates 3, 4, 7, 8 are bright yellow, mobile oils, in contrast to simple acylphosphonates which are typically colorless. Conversion of the α-diazomethylene precursor to carbonylbisphosphonate essentially reverses polarity at carbon, as reflected in the $^{31}$P NMR resonances which undergo an upfield shift of $\Delta\delta$=17-19 ppm (conversion to hydrate produces a downfield shift of $\Delta\delta$=20 ppm).

The synthetically versatile ketone group in α-keto bisphosphonate esters 4, and similar α-keto phosphonates such as phosphonoglyoxylates (3), phosphonoglyoxylamides (7) and α-keto phosphonophosphinates (8) could provide a convenient entry to a wide range of new α-substituted bisphosphonates and related system via nucleophilic addition chemistry. Indeed, it could be used to prepare any bisphosphonate possessing a particular utility or desirable property requiring introduction of a specific "R" group. It could also be extended to preparation of analogous bifunctional phosphonates such as phosphonoacetates, phosphonoacetoamides and phosphinophosphonates One advantage of this approach in preparation of bone active agents is that an α-hydroxy group is generated with introduction of the R moiety:

It should also be pointed out that the well known synthetic versatility of the ketone function can be exploited to form many other types of phosphonates. As one of many possible examples, we can mention the classic reductive amination reaction which could provide α-amino bisphosphonates of the class compounds McKenna et al. showed that carbonyl bisphosphonates 4 exhibit moderate HIV-reverse transcriptase (Ki=1.8 μM) whereas the α,β-methylene bisphosphonate was non inhibitory (26). This led us to consider the possibility of novel carbonyl bisphosphonate nucleotide analogues in which the α,β oxygen is replaced by a carbonyl, introducing a highly electron-deficient ketone group, which might be reactive to a neighboring nucleoside.

Accordingly, the present invention also provides a method of preparing a nucleotide analog, comprising the steps of (1) forming a monosalt of an α-diazomethylene bisphosphonate; and (2) coupling a nucleoside and the monosalt to form a nucleotide analog having formula VII:

wherein R1, R2 and R4 are each independently alkyl or aryl and R3 is a nucleosidyl moiety joined to the bisphosphonate via a 5'ester linkage.

A preferred method for forming the monosalt is by monodealkylating a tetralkyl ester of the α-diazomethylene bisphosphonate using sodium iodide. The coupling reaction may then be conducted by forming a reaction mixture of the free acid, the nucleoside and either; (1) (Benzotriazol-1-yloxy) tripyrrolidinophosphonium hexafluorophosphate (pyBOP) and diisopropylethylamine (DIEA), or (2) triphenyl phosphine (PPh$_3$) and diisopropyl azodicarboxylate (DIAD). The latter Mitsunobu coupling is preferred over the pyBOP method.

Figure 1:
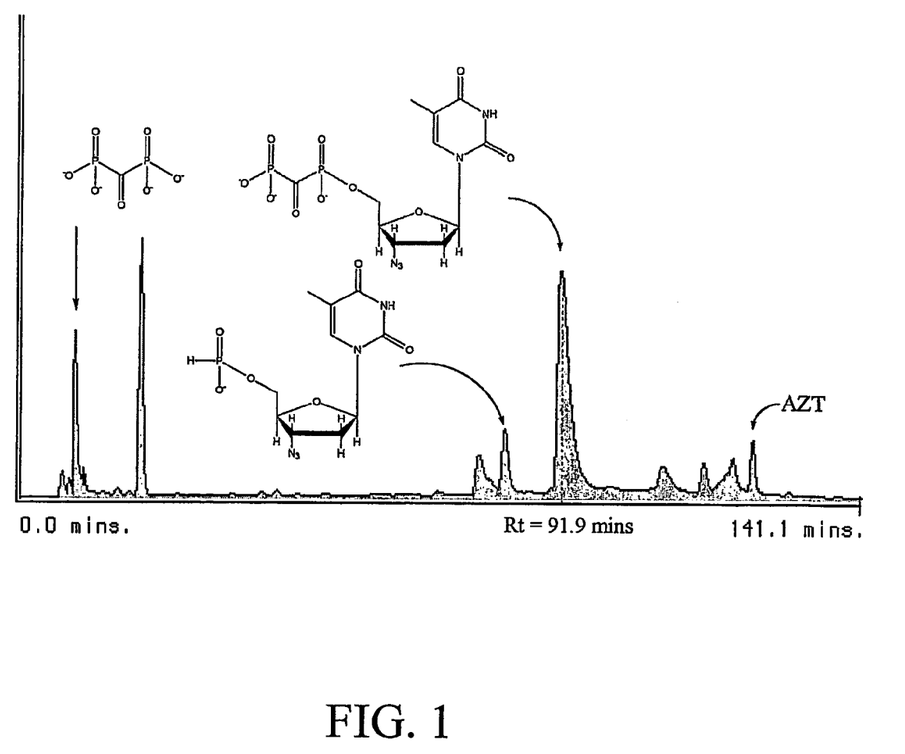
FIG. 1 shows isolation of AZT 5'-carbonylbisphosphonate from the reaction mixture by reverse phase HPLC.

The method may further comprise the step of oxidizing the diazomethylene bisphosphonate to form a carbonylbisphosphonate. As shown in FIG. 1 the carbonylbisphosphonate analog of a nucleotide can be isolated from the reaction mixture by preparative HPLC.

As a demonstration compound, we chose AZT-5'-carbonyl bisphosphonate, 13a. Our successful route to 13a, which exploits our recent discovery of practical methods to synthesize carbonylbisphosphonate tetraesters (40), is outlined in Scheme 2.

The starting tetramethyl diazomethylenebisphosphonate is readily available by diazo transfer from an aromatic sulfonyl azide to tetramethyl methylenebisphophonate in the presence of a base.

Monodemethylation of dimethyl diazobenzylphosphonate by sodium iodide in acetone proved easily adaptable to synthesis of the monosodium bisphosphonate trimethyl ester 10a by the simple expedient of using less than one equivalent of sodium iodide in portions (0.5, 0.25, 0.13 eq.), which minimized formation of the symmetrical disodium salt byproduct 10b. Conversely, the latter compound was readily obtained by using an excess of iodide.

Figure 2:
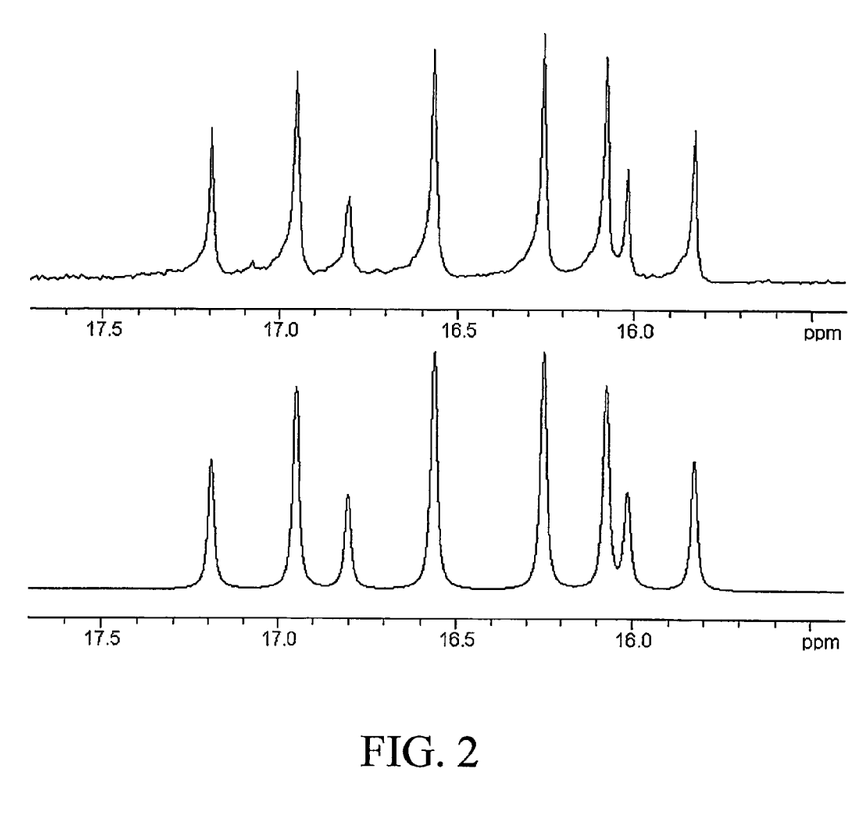
FIG. 2 shows the {$^1$H} $^{31}$P NMR of AZT trimethyl ester recorded at 202 MHz (top) and simulated (bottom)

We examined two different approaches to couple the monosalt 11 with the 5'-OH of AZT. Use of PyBOP gave only a modest yield (25%, NMR) of the nucleotide triester analogue 12. In contrast, under Mitsunobu conditions, the coupling reaction proceeded quantitatively (NMR). Success in this reaction was critically dependent on a) the choice of solvent system and b) maintaining perfectly anhydrous reaction conditions. Pure 12 was conveniently and rapidly isolated by PCFTLC on silica gel, the yield being somewhat reduced by demethylation on this chromatographic medium. Conjugation of the bisphosphonate with AZT generates a new R/S chiral center at Pα, resulting in diastereotopic doubling of the $^{31}$P NMR PαPβ ab multiplet (FIG. 2).

Figure 3:
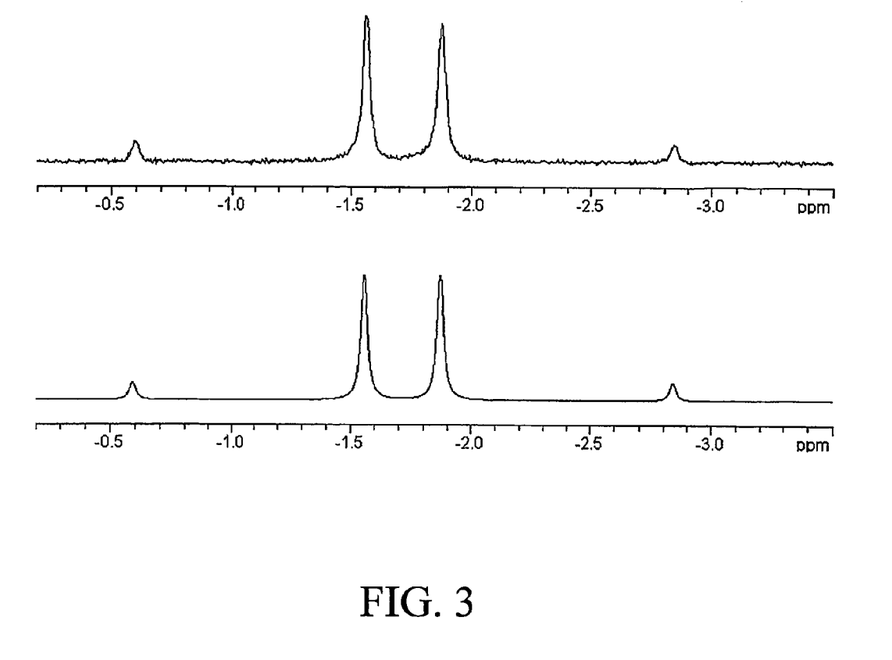
FIG. 3 shows {$^1$H} $^{31}$P NMR of AZT-P—CO—P, recorded at 202 MHz (top) and simulated (bottom)

Silyldealkylation of dialkyl phosphonates with BTMS followed by mild, rapid hydrolysis provides a facile path to the corresponding acids (27) and is generally compatible with alkyl or aryl ketones and esters (28). However, it was previously found that the unusually electrophilic carbonyl group in triethyl α-oxophosphonoacetate (triethyl phosphonoglyoxylate) tended to react with BTMS, whereas the α-diazo precursor of this compound cleanly underwent BTMS silyldeethylation without affecting the diazo group. The resulting P,P-bis(trimethylsilyl) C-ethyl triester ester could be oxidized in refluxing benzene by Rh$_2$(OAc)$_4$-propylene oxide, and the distillable ketone silyl ester was then hydrolysis of the bis (trimethylsilyl ester) with water However, initial formation of the highly reactive ketone led to problematic side reactions when BTMS was used in the second step. Accordingly, the three methyl groups of 12 were first removed by BTMS, and silyl ester hydrolysis, diazo oxidation was carried out on the resultant intermediate in situ with t-butyl hypochlorite, 3 eq. of water in a one pot process. The Rh$_2$(OAc)$_4$-propylene oxide system is ineffective in oxidizing diazobisphosphonates. Removal of unreacted BTMS after the first step without premature hydrolysis of the silyl ester function was essential for the success. Ketone formation was extremely rapid, characterized by a sudden appearance of a bright yellow color with gas evolution (N$_2$). Another important reaction parameter was the presence of a controlled excess of water. Under perfectly anhydrous conditions, the reaction was slow and gave α-chlorinated side product. Also important was a prompt adjustment of the reaction pH to slightly above neutral (7.5) the trianions 13a is relatively stable, the free α-carbonylbisphosphonic acid moiety is likely to decompose. The $^{31}$P NMR showns in FIG. 3 reveals an unusual high coupling constant ($^2$J$_{PP}$=196 Hz) for this kind of structure.

Some of the advantages of the foregoing synthetic route include: 1) the bisphosphonate-nucleoside Mitsunobu-type coupling step maximizes yield and convenience by Me protection of ¾ phosphonic acid groups; 2) in a rapid and mild, one-pot process, regioselective BTMS silyldemethylation (the 5'-methylene ester link is left intact), is followed by treatment with t-butyl hypochlorite/water which deprotects the three phosphonic acid groups while simultaneously converting the α-diazo group to a ketone; 3) subsequent neutralization with the base of choice provides the crude desired salt directly, without the necessity of cation exchange; 4) the product is readily purified by semi-prep HPLC followed by lyophilization.

A remarkable property of the α-ketone bisphosphonate derivative 13a is the pH-dependant reactivity of its ketone group, which can be reversibly converted to hydrate 13b as the pH is lowered (Scheme 3).

Scheme 3

13a          13b

Figure 4:
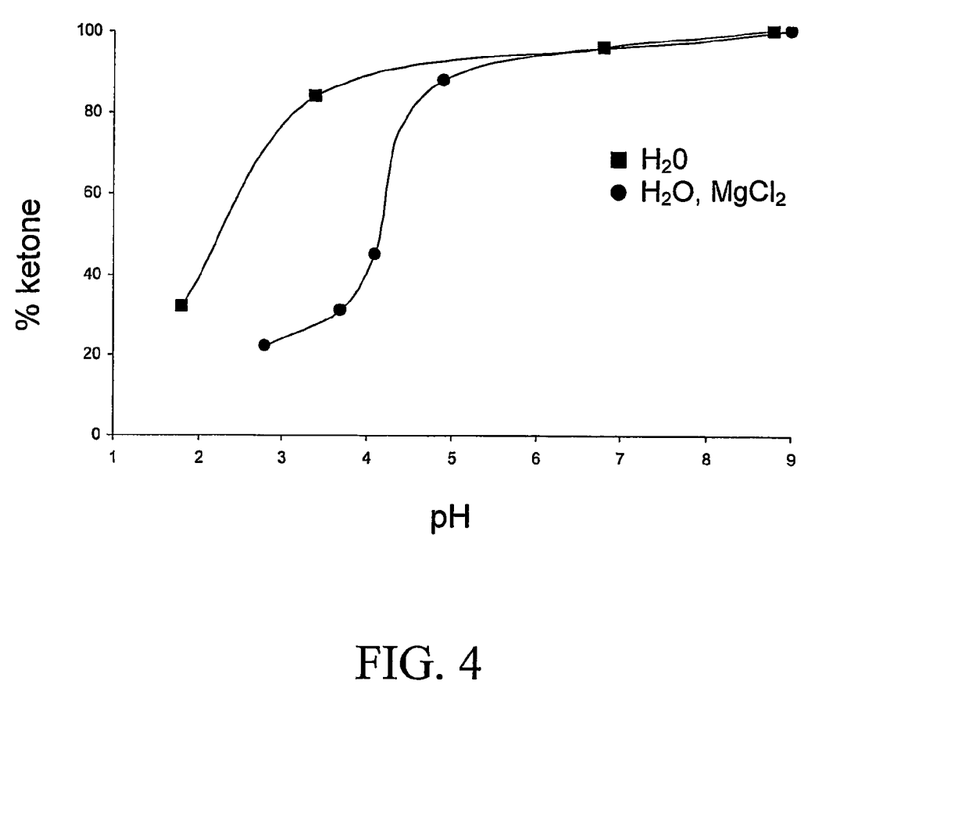
FIG. 4 shows the effect of pH and Mg+2 on the ketohydrate equilibrium of AZT 5'-carbonylbisphosphonate.

The ketone 13a and hydrate forms 13b are simultaneously detectable by $^{31}$P, and also via the visible absorbance (420 nm) of the ketone chromophore (yellow). At low pH, the hydrate form 13b predominates, the phosphorus NMR peak shifting from −2 to 15 ppm. The reaction is reversible, the ketone reforming as the pH is increased. The pH at which 50% of the ketone is transferred to its hydrate form ('pK') is 2.2 (rt, 10$^{-7}$M in D$_2$O). This unequivocally coincides with the protonation of the phosphonate function. Upon addition of MgCl$_2$, the apparent 'pK' of the equilibrium shifts by nearly 2 pH units towards left to reach 4.2 (FIG. 4).

The ketone 13a has reduced polarity due to the three negative charges on the neighboring phosphonate oxygens at high pH predominates in water. As the pH is decreased, protonation of the phosphonate bases decreases this electrostatic desactivation, and the ketone, electron-deficient due to two α-phosphonate groups, becomes increasingly reactive, shifting the ketone-hydrate equilibrium to the hydrate form. Rasanen et al. have shown in a series of ab initio calculations that methylene bisphosphonate and α,α-dichloro methylenebisphosphonate have the ability to form a bi and tridental complexes with one or two magnesium(II) metals in aqueous solution (29-32). We assume that similar complexes are formed in our models, allowing the ketone to be more sensitive to nucleophilic attacks.

Recently, Yanachov et al. (33) reported the synthesis of similar nucleoside analogues, with a guanidine base. Their method however differs from ours by using a direct coupling of the protected nucleoside with carbonyl bis and trisphosphonate with a respective yield of 93 and 17%.

EXAMPLES

I. Example 1

Synthesis of α-Keto Phosphonates

All reagents were AR grade from Sigma-Aldrich, Inc. NMR (Bruker AMX %500) spectra were referenced to tetramethylsilane ($^1$H, $^{13}$C) or external 85% $H_3PO_4$ ($^{31}$P). Elemental analysis provided by Galbraith Labarotaries Inc.

A. α-Diazophosphonates

α-Diazophosphonates were obtained from corresponding methylenephosphonates as previously described. (34)

Compound 5 (>97%): $^1$H NMR ($CDCl_3$): 0.9 (t, 6H, $CH_3CH_2O$—), 2.6 (s, 6H, $CH_3N$), 3.7 (q, 4H, $CH_3CH_2O$—). $^{31}$P NMR ($CDCl_3$): 13.2 (s). $^{13}$C NMR ($CDCl_3$): 15.0 (d, $CH_3CH_2O$—), 36.3 (s, $CH_3N$), 51.5 (d, $^1J_{cp}$=219.05 Hz, $C=N_2$), 62.3 (s, $CH_3CH_2O$—), 161.4 (d, $^2J_{cp}$=10.3 Hz, $C=O$). MS: calcd=249.09 g/mol; found=249 g/mol.

Compound 6 (>97%): $^{31}$P NMR ($CDCl_3$): 14.1 (d, $^2J_{Pp}$=32.53 Hz, P(O)(OEt)2), 26.0 (d, $^2J_{pP}$=32.54 Hz, P(O)(OEt)Ph).

B. α-Ketophosphonates

1. Synthesis and Purification of Dimethylaminooxalyl Phosphonic Acid Diethyl Ester (α-Keto PAmide), (7) from Diazo PAmide (5) and Rhodium (II) Perfluorobutyramide ($Rh_2(NHCOC_3F_7)_4$)

In a 500 mL 3 neck rb flask equipped with a magnetic stirrer, a condenser with Ar inlet/outlet at its top, thermometer, and addition funnel, was placed 150.4 mg (0.143 mmol, 2.74×10$^{-3}$ eq.) $Rh_2(NHCO_3F_7)_4$, and 23.0 mL (0.202 mol, 5.05 eq.) styrene oxide in 150.0 mL of benzene. The navyblue solution was left to stir for 30 min to allow for complete dissolution of the catalyst. Diazo PAmide (5, 10.0 g, 0.040 mol, 1.0 eq., yellow solution) was dissolved in the addition funnel with 50.0 mL benzene. The dropwise addition of the diazo derivative was started, the reaction mixture adopted bright, clear red color. Evolution of gas was observed. After completion of the reaction (about 2 h 30 min, indicated by $^{31}$P NMR), the mixture was concentrated under vacuum. When no more boil off was observed, 30.2 g of residue was remaining inside the flask, more than twice the expected amount. The residue was transferred inside e glove box, where the high vacuum distillation apparatus was assembled. Outside the glove box, the distillation column was connected to the high vacuum system and distillation was started. In about 1 h, 3 fractions were collected. The distillation yielded 6.64 g (54%, fraction 2 and 3) of a bright yellow liquid, α-keto PAmide (>97%): bp 69-71° C. (0.002 mmHg). $^1$H NMR ($CDCl_3$) δ 4.04 (m, 4H, $CH_3CH_2O$), 2.78, 2.76 (2s, 6H, $N(CH_3)_2$), 1.11 (1, 6H, $CH_3CH_2O$). $^{13}C\{^1H\}$NMR ($CDCl_3$) δ 198.05 (d, $^1J_{cp}$=17.2 Hz, P(O)C(O)C(O)), 164.25(d, $^2J_{cp}$=65.9 Hz, P(O)C(O)C(O)), 64.03 (d, $^2J_{cp}$=6.7 Hz, $CH_3CH_2O$), 35.92, 34.02 (2s, $N(CH_3)_2$), 15.71 (d, $^3J_{CP}$=6.1 Hz $CH_3CH_2O$). $^{31}P\{^1H\}$ NMR ($CDCl_3$) δ −2.31 (p, $^3J_{PH}$=8.0 Hz) IR (cm$^{-1}$) 2986, 2938 (m, $CH_3$, $CH_2$), 1658 (broad vs, C=O), 1266 (vs, P=O), 1023 (vs, P—O—C). Elemental analysis: Calcd: C 40.51%, H 6.80%, N 5.91%; Found: C 40.65%, H 7.05%, N 6.09%.

2. Synthesis and Purification of Tetraisopropyl Carbonylbisphosphonate (α-Keto TIPMDP, 4), from Diazo TIPMDP (2) and $Rh_2(NHCOC_3F_7)_4$ Inside the glove box ($N_2$ atm.), a 250 mL 3 neck rb flask equipped with a magnetic stirrer was loaded with 250.0 mg (0.24 mmol, 0.010 eq.) $Rh_2(NHCOC_3F_7)_4$, and 14.5 mL (0.120 mol, 5.2 eq.) 1,2-epoxyhexane in 90.0 mL toluene. Also inside the glove box, an addition funnel was loaded with 8.67 g (0.023 mol, 1 eq.) diazo TIPMDP (2) in 30 mL toluene. Outside the glove box, and under flow of UHP Ar, the 250 mL rb flask was equipped with a condenser with Ar Inlet/outlet at its top, a thermometer, and the addition funnel containing the diazo solution. The catalyst solution was heated to 93° C., the solution turns navy-blue. Dropwise addition of the diazo solution was started. After about 18 h, the reaction was completed (determined by $^{31}$P NMR). The solvent and the epoxide were easily removed under vacuum, inside the glove box. The distillation apparatus was also assembled inside the glove box, then transferred outside to be connected to the high vacuum line. High vacuum distillation yielded 4.96 g (60%, fraction 2 & 3) of a bright yellow liquid. α-keto TIPMDP 4>95%): bp 79-81° C. (0.002 mmHg). $^1$H NMR ($CDCl_3$) δ 4.75 (m, 4H, $(CH_3)_2CHO$). 1.28, 1.27 (2d, 24H, $(CH_3)_2$ CHO). $^{13}$C NMR ($CDCl_3$) δ 216.38 (t, $^1J_{CP}$=149.5 Hz, C=O), 73.66 (large s, $(CH_3)_2CHO$), 24.02, 23.51 23.51(2s, $(CH_3)_2(CHO)$. $^{31}P\{^1H\}$ NMR ($CDCl_3$) δ −5.91 (s). $^{31}$P NMR ($CDCl_3$), (t, $^3J_{PH}$=3.5 Hz). IR (cm$^{-1}$) 2984, 2937 (s, $CH_3$, CH), 1665 (m, C=O), 1266 (vs, P=O), 995 (broad vs, P—O—C). Elemental analysis: Calcd: C 43.58%, H 7.88%; Found: C 43.75%, H 8.04%.

3. Synthesis and Purification of Triethyl Phosphonoglyoxylic Acid (α-Keto TEPA,3) from Diazo TEPA (1) and $Rh_2(NHCOC_3F_7)_4$ The following reaction was performed inside a glove box ($N_2$ atm.). In a 100 mL rb flask equipped with a condenser with a moisture trap at its top, was placed 49.4 mg (46.9×10$^{-3}$ mmol, 1.7×10$^{-3}$ eq.) $Rh_2(NHCOC_3F_7)_4$ with 12.07 mL (0.140 mol, 5.0 eq.) 1,2-epoxybutane in 63 mL, benzene. The purple catalyst solution was heated to 50° C. Dropwise addition of diazo TEPA (1, 7.01 g, 0.028 mol, 1.0 eq.) in 20 ml. benzene was started using and addition funnel connected to the top of the condenser. The solution turns first pinkish, then bright yellow, and evolution of gas was observed. After 10 h, 50% of diazo TEPA (1) remained in the solution, thus 17.3 mg (16.4×10$^{-3}$ mmol, 2.3×10$^{-3}$ eq.) $Rh_2(NHCOC_3F_7)_4$ in 1.0 mL 1,2-epoxybutane was added to the mixture, heating was stopped, and the reaction was left overnight. At the end of the reaction, the color was yellow-orange. The solvent, and excess epoxide were evaporated under vacuum inside the glove box. The distillation apparatus was assembled inside the glove box and transferred outside to be connected to the high vacuum line. High vacuum distillation yielded 3.52 g (53%, fraction 1 & 2) of a bright yellow liquid. α-keto TEPA (3>99%): bp 58-60° C. (0.002 mm Hg). $^1$H NMR ($CDCl_3$) δ 4.29 (q, 2H, $CH_3CH_2OC$), 4.22 (m, 4H, $(CH_3CH_2O)_2P$), 1.28 (t, 9H, $CH_3CH_2O$). $^{13}C\{^1H\}$ NMR ($CDCl_3$) δ 193.54 (d, $^1J_{CP}$=183.1 Hz, P(O)C(O)C(O)), 159.19 (d, $^2J_{CP}$=78.6 Hz, $C(O)OCH_2CH_3$), 64.60 (d, $^2J_{CP}$=6.1 Hz, $(CH_3CH_2O)_2P$), 63.07 (s, $CH_3CH_2OC$), 16.12 (d, $^3J_{CP}$=5.7 Hz, $(CH_3CH_2O)_2$ P), 13.67 (s, $CH_3CH_2OC$). $^{31}P\{^1H\}$ NMR ($CDCl_3$) δ −2.57 (s). $^{31}$P NMR ($CDCl_3$) δ −2.57 (p, $^3J_{PH}$=8.2 Hz). IR (cm$^{-1}$) 2987, 2939 (m, $CH_3$, $CH_2$), 1739 (broad vs, C=O), 1271 (broad vs, C—O—C, P=O), 1026 (vs, P—O—C).

4. Synthesis Diethyl [(Ethoxyphenylphosphinyl)carbonyl]phosphonate α-Keto PPP, 8) from Diazo PPP(6) and $Rh_2(NHCOC_3F_7)_4$ The following reaction was performed inside a glove box ($N_2$ atm.). In a 10 mL rb flask equipped with a condenser with a moisture trap at its top, were placed 11.0 mg ($10.4 \times 10^{-3}$ mmol, $8.8 \times 10^{-3}$ eq.) $Rh_2(NHCOC_3F_7)_4$ with 0.640 mL (7.43 mmol, 6.2 eq.) 1,2-epoxybutane in 3 mL benzene. The purple catalyst solution was heated to reflux. Dropwise addition of diazo PPP (6, 0.412 g, 1.19 mmol, 1.0 eq.) in 2 mL benzene was started using a Pasteur pipette. The solution goes from pinkish, to orange, to red and finally brownish. Evolution of gas was observed right when the addition started. The reaction was followed by $^{31}P$ NMR, after 5 h 40 min only 23% conversion is observed. After almost 7 h, more catalyst (30.0 mg, $28.4 \times 10^{-3}$ mmol, $23.5 \times 10^{-3}$ eq.) was added to the mixture along with more epoxide (1.0 mL, 11.6 mmol, 9.7 eq.). One hour after the last addition, 44% conversion was observed. Before the end of the reaction more catalyst and epoxide were added bringing the proportions to: 66.4 mg ($63.0 \times 10^{-3}$ mmol, $52.6 \times 10^{-3}$ eq.) of $Rh_2(NHCOC_3F_7)_4$ and 2.64 mL (30.6 mmol, 26.0 eq.) 1,2-epoxybutane in 7 mL of benzene. After about 24 h of reaction, α-keto PPP (8) seemed to be the major product, but diazo PPP (6) was still present in the mixture along with some decomposition products. 2.5 mL (21.9 mmol, 4.6 eq.) of styrene oxide is added to the mixture to drive the reaction. 48 h after the reaction started, no more diazo compound is left inside the mixture. The reaction was stopped and high vacuum distillation was attempted. The product underwent massive decomposition during distillation. α-keto PPP (8, 20-40%): $^{31}P\{^1H\}$ NMR (benzene) δ 18.42 (d, $^2J_{PP}$=217.6 Hz, 1P, Ph($CH_3CH_2O$)P(O)), −2.61 (d, $^2J_{PP}$=217.6 Hz, 1P, $(CH_3CH_2O)_2P(O)$).

5. Synthesis of Diethyl Benzoylphosphonate (10) from (Diazophenylmethyl)phosphonic Acid Diethyl Ester (9) and $Rh_2(NHCOC_3F_7)_4$ $EtO_2P(O)C(N_2)Ph$ (9, 304.0 mg, 1.19 mmol, 1.00 eq., bright red) was dissolved in 0.500 mL commercial anh. benzene in a vial with a Teflon septum screw cap. In a 5 mL rb flask equipped with a condenser, Ar inlet/outlet, and a side port with a Teflon septum screw cap, was prepared a solution containing 4.20 mg ($3.98 \times 10^{-3}$ mmol, $3.3 \times 10^{-3}$ eq.) of $Rh_2(NHCOC_3F_7)_4$ and 0.128 g (1.77 mmol, 1.5 eq.) of 1,2-epoxybutane in 1.00 mL commercial anh. benzene. The diazo derivative solution was added to the catalyst solution. First, the color was very dark, but quickly changed to clear reddish. Evolution of gas was observed. The conversion was quantitative (>99% by $^{31}P$ NMR), and was completed in less than 5 min. 261.0 mg (91%) of crude compound was recovered after concentration of the solvent. Centrifugal chromatography was attempted but did not yield satisfactory results due to the sensitivity of the product to moisture. $EtO_2P(O)C(O)Ph$ (10):$^1H$ NMR ($CDCl_3$) δ 8.06 (d, 2H, ortho-H), 7.42 (t, 1H, para-H), 7.29 (t, 2H, meta-H), 4.07 (m, 4H, $OCH_2CH_3$), 1.17 (td, 6H, $OCH_2CH_3$). $^{13}C\{^1H\}$ NMR ($CDCl_3$) δ 198.46 (d, $^1J_{CP}$=174.8 Hz, C=O), 135.08 (d, $^2J_{CP}$=64.14 Hz, arom-$C_1$), 134.28 (s, para-C), 129.27 (s, meta-C), 128.37 (s, ortho-C), 63.47 (d, $^2J_{CP}$=6.5 Hz, $CH_3CH_2O$), 15.86 (d, $^3J_{CP}$=5.5 Hz, $CH_3CH_2O$). $^{31}P\{^1H\}$ NMR ($CDCl_3$) δ −0.57 (s). $^{31}P$ NMR ($CDCl_3$) δ −0.57 (p, $^3J_{PH}$=8.1 Hz). IR ($cm^{-1}$) 3066-2900 (m-w, $CH_3$, $CH_2$, arom-CH), 1655 (vs, C=O), 1257 (vs, P=O), 1050, 1022 (vs, P—O—C). $EtO_2P(O)C(N_2)Ph$ (5a): $^1H$ NMR ($CDCl_3$) δ 7.28 (t, 2H, aromatic meta-H), 7.11 (d, 2H, aromatic ortho-H), 7.06 (t, 1H, aromatic para-H), 4.15, 4.06 (q, 2H; q, 2H; $OCH_2CH_3$), 1.26 (t, 6H, $OCH_2CH_3$). $^{13}C\{^1H\}$ NMR ($CDCl_3$) ν̈ 128.70 (s, meta-C), 126.14 (d, $^2J_{CP}$=9.8 Hz, arom-$C_1$), 124.61 (s, para-C), 122.14 (d, $^3J_{CP}$=4.3 Hz, ortho-C), 63.33 (d, $^2J_{CP}$=4.5 Hz, $CH_3CH_2O$), 50.04 (d, $^1J_{CP}$=226.1 Hz, C=$N_2$), 15.59, 15.58 (2d, $^3J_{CP}$=4.3 Hz, $CH_3CH_2O$). $^{31}P\{^1H\}$ NMR ($CDCl_3$) ν̈ 17.92 (s). $^{31}P$ NMR $\{CDCl_3\}$ ν̈ 17.92 (p, $^3J_{PH}$=8.2 Hz). IR ($cm^{-1}$) 3066-2900 (m-w, $CH_3$, $CH_2$, arom-CH), 2079 (vs, C=N=N), 1258 (s, P=O), 1018 (s, P—O—C).

C. Epoxide Effect on Rh Oxidations

Four epoxides were tested as oxygen donors to the presumed 5-Rh carbenoid intermediate: 7 eq. of propylene oxide, 1,2-epoxybutane, 1,2-epoxyhexane or styrene oxide. After 15 hr in benzene at rt using the most active catalyst [$Rh_2(NHCOC_3F_7)_4$ ($0.55 \times 10^{-3}$ mol %)], reaction was still incomplete with the alkyl epoxides, but was complete with styrene oxide in ~½ hr.

In contrast, 1,2-epoxyhexane and styrene oxide with the same catalyst gave very similar rates of oxygen transfer to 2-Rh (overnight, 100° C. in toluene; NR at rt).

D. Ligand Effect on Rh Oxidations

Replacement of the "standard" rhodium catalyst, $Rh_2(OCOCH_3)_4$, by $Rh_2(NHCOC_3F_7)_4$ dramatically accelerates the oxidations.

Thus, 3 was formed within minutes from 1 (rapid evolution of $N_2$) at rt using the new catalyst, vs. 16 hr at 80° C. with the standard one.

Both the P—C(=$N_2$)—P substrates (2, 6), which are completely unreactive to oxidation using $Rh_2(OCOCH_3)_4$, were readily converted to the corresponding α-keto products (4, 8) using $Rh_2(NHCOC_3F_7)_4$.

E. Relative Ketone Reactivity

Preliminary results on the relative reactivity of compounds 3, 4 and 7 to the $H_2O$ nucleophile in EtOAc were obtained under competitive conditions (0.08:0.08:0.07 mmol substrate).

The $H_2O$ (total, 0.41 mmol) was added in small aliquots over a period of 4 hours. The reaction was followed by $^{31}P$ NMR.

The results indicate the following order of reactivity: 3>4>7.

II. Example 2

Synthesis of 5'-Carbonylbisphosphonate

We, report here synthesis and characterization of the first example of a new class of nucleotide analog, in which the α,β-phosphoric anhydride oxygen of the 5'-diphosphate moiety is replaced by a reactive carbonyl group: the carbonylbisphosphonate analog of 3'-azido-3'desoxythymidine 5'-diphosphate, 13. The structures of 13 and its diazomethylenebisphosphonate precursor 12 were confirmed by $^1H$, $^{13}C$ and $^{31}P$ NMR, and high-resolution mass spectrometry. The ketone and hydrate forms of 13 are simultaneously detectable by $^{31}P$, and also via the visible absorbance (420 nm) of the ketone chromophore. At low pH, the hydrate form predominates, the phosphorus NMR peak shifting from −2 to 15 ppm. The reaction is reversible, the ketone reforming as the pH is increased. Addition of $Mg^{2+}$ shifts the 'pK' of the equilibrium by nearly 2 pH units. (See FIG. 4).

A. Nucleoside—Bisphosphonate Coupling

1. Materials and Methods

NMR spectra were obtained on a Bruker AM360 unless otherwise indicated. High resolution mass spectra were obtained at the UC Riverside Regional Mass Spectrometry Facility on a VG ZAB2SE instrument with Opus V3.1 and DEC 3000 Alpha Station operated in FAB anions modes. Gradient HPLC purification and analysis were carried out with a Rainin Dynamax SD-200 solvent delivery system (dual PEEK pumps), equipped with a Dynamax UV-DII UV-Visible absorbance detector. Preparative centrifugal flow thin-layer chromatography (PTFTLC) was performed on an Analab Cyclograph operated at 1,000-1,400 rpm with a flow of 1 ml/min through silica gel rotors with UV detection of eluting bands.

Acetone, ethyl acetate, dichloromethane and dioxane solvent, respectively 99.9, 99.5, 99.9 and 99.3% purity, were obtained from VWR. They were all distilled with calcium hydride except dioxane, which was refluxed with sodium metal. DOWEX© 50W*200-8 ion-exchange resin, DIAD (95%), PPh3 (99%) and tBuOH (99%, kept under nitrogen atmosphere) were obtained from Aldrich. DIAD was distilled under reduced pressure (108 C at 20 μm of mercury). Tert butyl hypochlorite was prepared from tBuOH and bleach (Chlorox). Tetramethyl diazomethylene bisphosphonate was available from previous synthetic step.

2. Sodium Trimethyl Diazomethylenebisphosphonate, 11

Tetramethyl diazomethylenebisphosphonate 10 (36) (1.04 g, 4 mmol) was dissolved in dry acetone (4 mL) and sodium iodide (0.3 g, 2 mmol) in dry acetone (2 mL) was added dropwise over 10 min. After 50 min. at rt, a white precipitate appeared and two additional portions of sodium iodide in acetone (0.16 g, 1 mmol and 0.08 g, 0.5 mmol) were added. The product was washed with acetone and dried under reduced pressure, yield is 0.71 g (74%). $^1$H NMR (CDCl$_3$): δ 3.83 (6H, d, J=12 Hz), 3.63 (3H, d, J=12 Hz). $^{31}$P NMR (CDCl$_3$): δ 7.79 (1P, d, $^2J_{PP}$=32 Hz), 24.59 (1P, d, $^2J_{PP}$=32 Hz).

3. Trimethyl 3'-Azido-3'-deoxythymidine 5'-diazomethylenebisphosphonate, 12 a. A. Via PyBOP as a Coupling Agent (35):

Trimethyl diazo methylene bisphosphonate, 11 (75 mg, 0.29 mmol) dissolved in 5 ml of methanol was stirred with DOWEX© 50W*200-8 ion-exchange resin (1 g, 25 meq) for one h. After filtration, the filtrate was evaporated under vacuum to constant weight, and the residue taken up in DMF (8 ml). AZT (100 mg, 0.38 mmol) was dissolved in the mixture and pyBOP (197 mg, 0.38 mmol) was added, followed immediately by addition of diisopropylethylamine (DIEA, 130 mg, 1.01 mmol). After 4 h, the reaction was checked by $^{31}$P NMR.

b. B. Via Mitsunobu Coupling (36, 37):

Trimethyl diazo methylene bisphosphonate, 11 (163 mg, 0.61 mmol) was converted to free acid by similar procedure (DOWEX); the residue being taken up in dioxane (8 ml). AZT (224 mg, 0.84 mmol) was dissolved in the mixture and triphenyl phosphine (220 mg, 0.84 mmol) was added, followed immediately by dropwise addition of diisopropyl azo dicarbonyl (DIAD, 170 mg, 0.84 mmol) in 2 ml of dioxane over 30 min. After 4 h, the solvent was removed by rotatory evaporation at reduced pressure, and the residue purified by PCTLC (4 mm silica gel plate, eluent diethyl ether: methanol, 9:1). The product was a viscous liquid of the two diastereoisomers (148 mg, 49%). $^1$H NMR (CDCl$_3$): δ 1.93 (3H, s, C5-C$\underline{H}_3$), 2.40, (2H, m, H2'), 3.78-3.89 (9H, 3d, J=3 Hz, POC$\underline{H}_3$), 4.01 (1H, s, H4'), 4.26-4.48 (3H, m, H5' and H3'), 6.20 and 6.22 (1H, 2t, J=6 Hz, H1'), 7.40 and 7.44 (1H, 2s, H6), 8.43 (s, N$\underline{H}$). $^{13}$C NMR (CD$_3$OD): δ 12.40 and 12.42 (C7, m), 37.45 and 37.60 (C2'), 54.68-54.96 (3 POC$\underline{H}_3$, m), 61.53 (C3'), 67.53 and 67.83 (C5', m), 83.35, 83.41 ($\underline{C}$=N$_2$, m), 86.52 (C4', m), 86.59 (C1', m), 111.94 (C5), 137.82 and 138.14 (C6, m), 152.11 (C2), 166.20, 166.48 (C4). $^{31}$P NMR (CD$_3$OD, ref H$_3$PO$_4$): δ 1$^{st}$ diastereoisomer: 16.16 (d, $^2J_{pp}$=35.0 Hz), 16.66 (d, $^2J_{pp}$=35.0 Hz); δ 2$^{nd}$ diastereoisomer: 15.97 (d, $^2J_{pp}$=35.6 Hz), 17.06 (d, $^2J_{pp}$=35.6 Hz). MS (glycerol, positive ion FAB): Calcd for C$_{13}$H$_{23}$O$_9$N$_7$P$_2$—H$^+$:494 Found: 494.

4. 3'-Azido-3'-Deoxythymidine 5'-Carbonylbisphosphonate, 13 (26, 38, 39):

The diazo bisphosphonate AZT analogue, 12 (286 mg, 0.60 mmol) in 1 ml of CH$_2$Cl$_2$ under dry nitrogen was stirred with excess bromotrimethylsilane (BTMS, 459 mg, 3.00 mmol) for one h. Volatiles were removed under reduced pressure (N$_2$) and the residue dissolved in 4 ml of ethyl acetate. Upon addition of t-butyl hypochlorite (76 mg, 0.70 mmol) in 2 ml ethyl acetate containing a slight excess of water (20 μl, 1.20 mmol), the solution turned yellow and gas evolution (N$_2$, HCl) was observed. After 3 min, the solvent was evaporated, the residue dissolved in water and the pH quickly adjusted to 7.5 with NaHCO$_3$. Water was removed and the product was precipitated from methanbl/diethyl ether and purified by semipreparative reverse phase HPLC as a (tris)triethylammonium salt. HPLC: C-18 column, 21.4 mm diameter, 25 cm length, eluted with a triethyl ammonium-acetate in water/acetonitrile gradient 2-15%, 6 mL/mn, pH 7.5, UV detection at 266 and 210 nm, retention time 91.9 min, chromatogram shown in FIG. 1.

Lyophilization left a bright yellow solid (150 mg, 0.30 mmol, 50%). $^1$H NMR (D$_2$O, ext. ref. CDCl$_3$): δ 1.11 (t, J=8 Hz, C$\underline{H}_3$—CH$_2$—N), 1.76 (9H, σ, C5-C$\underline{H}_3$), 2.34 (2H, m, J=6 Hz, H2'), 2.91 (8H, q, J=8 Hz, CH$_3$—C$\underline{H}_2$—N), 4.04 (1H, s, H4'), 6.13 (1H, t, J=6 Hz, H1'), 7.65 (1H, s, H6). $^{13}$C NMR (D$_2$O, AcOH): δ 12.35 (C7), 38.05 (C2'), 62.62 (C3'), 67.09 (C5'), 85.03 and 86.54 (C1' and C4'), 113.64 (C5), 139.19 (C6), 153.60 (C2), 168.55 (C4). $^{31}$P NMR (D$_2$O, pH=7.5): δ −1.29 (1P, d, $^2J_{PP}$=196 Hz), −2.13 (1P, d, $^2J_{PP}$=196 Hz). HRMS (glycerol, negative ion FAB): Calcd for C$_{11}$H$_{14}$O$_{10}$N$_5$P$_2$: 438.0216. Found: 438.0220.

REFERENCES

The following references are incorporated herein by reference in their entirety.

1. Ebetino, F. H. Phosphorus, Sulfur Silicon Relat. Elem. 1999, 144-146, 9-12.
2. De Clercq, E. (2001) *Current Medicinal Chemistry* 8, 1543-1572.
3. De Clercq, E. (2002) *Nature Reviews Drug Discovery* 1, 13-25.
4. Hamilton, C. J., Roberts, S. M. and Shipitsin, A. (1998) *Chem. Commun.* (Cambridge) 1087-1088.
5. Balzarini, J., Haller-Meier, F., De Clercq, E. and Meier, C. (2001) *Antiviral Chemistry & Chemotherapy* 12, 301-306.
6. Daluge, S. M. and Wilson, J. D. (1996) *PCT Int. Appl.*; (Wellcome Foundation Limited, UK).Wo, 14 pp.
7. Schinazi, R. F. and Liotta, D. C. (1996) *PCT Int Appl.*; (Emory University, USA).Wo, 44 pp.
8. Parang, K., Wiebe, L. I. and Knaus, E. E. (2000) *Curr. Med. Chem.* 7, 995-1039.
9. Ohrui, H. and Mitsuya, H. (2001) *Curr. Drug Targets: Infect Disord.* 1, 1-10.
10. Vacca, J. P., Lin, J. H., Yeh, K. C., Chodakewitz, J. A., Deutsch, P. J. and Ju, W. D. (1999) *PCT Intl. Appl.*; (Merck & Co., Inc., USA).Wo, 56 pp.
11. Debyser, Z. and De Clercq, E. (1996) *Riv. Immunol. Immunofarmacol.* 16, 48-52.
12 Davisson, V. J., Davis, D. R., Dixit, V. M. and Poulter, C. D. (1987) *J. Org. Chem.* 52, 1794-1801.
13. McLennan, A. G., Taylor, G. E., Prescott, M. and Blackburn, G. M. (1989) *Biochemistry* 28, 3868-3875.

14. Watanabe, K. A., Pankiewicz, K. W., Goldstein, B. M. and Bell, J. E. (1994) *PCT Int. Appl.*; (Sloan-Kettering Institute for Cancer Research, USA; University of Rochester).Wo, 76 pp.
15. Lesiak, K., Watanabe, K. A., Majumdar, A., Seidman, M., Vanderveen, K., Goldstein, B. M. and Pankiewicz, K. W. (1997) *J. Med. Chem.* 40, 2533-2538.
16. Balzarini, J., Herdewijn, P., Pauwels, R., Broder, S. and De Clercq, E. (1988) *Biochem. Pharmacol.* 37, 2395-2403.
17. Guranowski, A., Starzynska, E., Gzik, L., Langston, S. P., Brown, P. and Blackburn, G. M. (1995) *Nucleosides Nucleotides* 14, 731-734.
18. Blackburn, G. M. and Langston, S. P. (1991) *Tetrahedron Lett.* 32, 6425-6428.
19. Blackburn, G. M., Kent, D. E. and Kolkmann, F. (1984) *J. Chem. Soc., Perkin Trans.* 1 1119-1125.
20. Burton, D. J., Pietrzyk, D. J., Ishihara, T., Fonong, T. and Flynn, R. M. (1982) *J. Fluorine Chem.* 20, 617-626.
21. McKenna, C. E.; Kashemirov, B. A. 2000, U.S. Pat. No. 6,147,245.
22. Cox, G. G.; Miller, D. J.; Moody, C. J.; Sie, E.; Kulagowski, J. J. Tetrahedron 1994, 50, 3195-3212.
23. Shapiro, E. A.; Dyatkin, A. B.; Nefedov, O. M. Russian Chemical Reviews 1993, 62, 485-509.
24. Brown, D. S.; Elliott, M. C.; Moody, C. J.; Mowlem, T. J.; Marino Jr., J. P.; Padwa, A. J. Org. Chem 1993, 59, 2447-2455.
25. McKenna, C. E.; Levy, J. N. J. Chem. Soc., Chem. Comm. 1989, 246-247.
26. McKenna, C. E., Kashemirov, B. A. and Li, Z.-M. (1999) *Phosphorus, Sulfur Silicon Relat. Elem.* 144-146, 313-316.
27. McKenna, C. E., Higa, M. T., Cheung, N. H. and McKenna, M. C. (1977) *Tetrahedron Lett.* 155-158.
28. McKenna, C. E. and Schmidhauser, J. (1979) *J. Chem. Soc., Chem. Commun.* 739.
29. Rasanen, J. P., Pohjala, E., Nikander, H. and Pakkanen, T. A. (1996) *J. Phys. Chem.* 100, 8230-8239.
30. Rasanen, J. P., Pohjala, E. and Pakkanen, T. A. (1996) *J. Chem. Soc., Perkin Trans.* 2 39-47.
31. Rasanen, J. P., Pohjala, E. and Pakkanen, T. A. (1994) *J. Chem. Soc., Perkin Trans.* 2 2485-2490.
32. Rasanen, J. P., Pohjala, E., Nikander, H. and Pakkanen, T. A. (1997) *J. Phys. Chem. A* 101, 5196-5204.
33. Yanachkov, I. B., Stattel, J. M. and Wright, G. E. (2001) *J. Chem. Soc., Perkin Trans.* 1 3080-3089.
34. Khare, A. B.; McKenna, C. E. Synthesis 1991, 405-406
35. Campagne, J.-M., Coste, J. and Jouin, P. (1995) *J. Org. Chem.* 60, 5214-5223.
36. Campbell, D. A. (1992) *J. Org. Chem.* 57, 6331-6335.
37. Campbell, D. A. and Bermak, J. C. (1994) *J. Org. Chem.* 59, 658-660.
38. Kashemirov, B. A., Roze, C. N. and McKenna, C. (2001) *XVth International Conference on Phosphorus Chemistry* PA017,
39. Kashemirov, B. A. and McKenna, C. (2002) *Topics Curr. Chem.* 220, 201-238.

What is claimed is:

1. A method of preparing an α-keto phosphonate of the formula the method comprising:
i) forming a reaction mixture comprising a rhodium(II) catalyst, an alkene oxide and an α-diazo phosphonate having formula IV:

wherein X is selected from the group consisting of —C(=O)OR3, —C(=O)N(R4)(R5), and —P(=O)(OR6)(R7), wherein R1, R2 R3, R4, R5 and R6 and each independently selected from the group consisting of alkyl, and aryl; R7 is selected from the group consisting of alkyl, aryl, and OR8, wherein R8 is selected from the group consisting of alkyl, aryl and nucleosidyl; and
ii) oxidizing the α-diazo phosphonate to form an α-keto phosphonate.

2. The method of claim 1 wherein the alkene oxide is selected from the group consisting of propylene oxide, 1,2-epoxybutane, 1,2-epoxyhexane and styrene oxide.

3. The method of claim 1 wherein X is —C(=O)N(R4)(R5) and the alkene oxide is styrene oxide.

4. The method of claim 1 wherein the catalyst is selected from the group consisting of $Rh_2(NHCOC_3F_7)_4$, $Rh_2(OCOCH_3)_4$, $Rh_2(NHCOCF_3)_4$, and $Rh_2(NHCOCH_3)_4$.

5. The method of claim 1 wherein the catalyst is $Rh_2(OCOCH_3)_4$ and X is —C(=O)N(R4)(R5).

6. The method of claim 1 wherein the catalyst is $Rh_2(NHCOC_3F_7)_4$.

* * * * *